(12) United States Patent
Fiser et al.

(10) Patent No.: US 11,435,355 B2
(45) Date of Patent: Sep. 6, 2022

(54) RESIDUE-BASED PHARMACOPHORE METHOD FOR IDENTIFYING COGNATE PROTEIN LIGANDS

(71) Applicant: ALBERT EINSTEIN COLLEGE OF MEDICINE, Bronx, NY (US)

(72) Inventors: Andras Fiser, New York, NY (US); Enghui Yap, Scarsdale, NY (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 1022 days.

(21) Appl. No.: 16/068,938

(22) PCT Filed: Jan. 4, 2017

(86) PCT No.: PCT/US2017/012089
§ 371 (c)(1),
(2) Date: Jul. 10, 2018

(87) PCT Pub. No.: WO2017/139044
PCT Pub. Date: Aug. 17, 2017

(65) Prior Publication Data
US 2019/0369097 A1    Dec. 5, 2019

Related U.S. Application Data

(60) Provisional application No. 62/293,026, filed on Feb. 9, 2016.

(51) Int. Cl.
G01N 33/574 (2006.01)
G16B 15/30 (2019.01)
G06F 3/14 (2006.01)

(52) U.S. Cl.
CPC ........... G01N 33/5748 (2013.01); G06F 3/14 (2013.01); G16B 15/30 (2019.02); *G01N 2500/00* (2013.01)

(58) Field of Classification Search
None
See application file for complete search history.

(56) References Cited

U.S. PATENT DOCUMENTS

| | | | |
|---|---|---|---|
| 2002/0099506 A1 | 7/2002 | Floriano et al. | |
| 2003/0148386 A1* | 8/2003 | Balaz | G16B 15/20 435/7.1 |
| 2004/0219542 A1* | 11/2004 | Houston | C07K 14/705 435/6.16 |
| 2005/0032138 A1 | 2/2005 | Lathrop et al. | |
| 2005/0053999 A1 | 3/2005 | Gough et al. | |
| 2011/0039808 A1* | 2/2011 | Desreumaux | A61P 25/04 546/156 |
| 2011/0263454 A1* | 10/2011 | Jonker | C12Q 1/6897 506/10 |
| 2013/0126417 A1 | 9/2013 | Ray et al. | |

(Continued)

OTHER PUBLICATIONS

PCT International Search Report and Written Opinion dated Mar. 17, 2017 for PCT International Patent Application No. PCT/US2017/012089, 9 pages.

(Continued)

*Primary Examiner* — Toan H Vu
(74) *Attorney, Agent, or Firm* — Amster, Rothstein & Ebenstein LLP

(57) ABSTRACT

A system and a method for identifying a cognate ligand molecules for known proteins.

20 Claims, 4 Drawing Sheets

(56) References Cited

U.S. PATENT DOCUMENTS

2016/0378912 A1* 12/2016 Ragno .................. G16C 20/60
    506/8
2020/0325203 A1* 10/2020 Kostenich .......... A61K 47/6923

OTHER PUBLICATIONS

Yap et al., "Functional clustering of immunoglobulin superfamily proteins with protein-protein interaction information calibrated Hidden Markov model sequence-profiles," Journal of Molecular Biology, Nov. 16, 2013, vol. 426, Issue 4, pp. 945-961.

* cited by examiner

RESIDUE-BASED PHARMACOPHORE METHOD FOR IDENTIFYING COGNATE PROTEIN LIGANDS

CROSS-REFERENCE TO RELATED APPLICATIONS

This application claims benefit of U.S. Provisional Application No. 62/293,026, filed Feb. 9, 2016, the contents of which are hereby incorporated by reference.

STATEMENT OF GOVERNMENT SUPPORT

This invention was made with government support under grant number ACI-1053575 awarded by the National Science Foundation. The government has certain rights in the invention.

BACKGROUND OF THE INVENTION

Throughout this application various publications are referred to. Full citations for the references may be found at the end of the specification. The disclosures of these publications are hereby incorporated by reference in their entirety into the subject application to more fully describe the art to which the subject invention pertains.

The immunoglobulin superfamily (IgSF) is one of the largest domain families in the human proteome (Lander et al., 2001). Excluding antibodies, the human proteome contains 477 cell-surface and secreted IgSF proteins (extracellular IgSFs') that regulate a broad spectrum of biological processes, ranging from neural development to immune response, primarily through specific cell-to-cell (trans) IgSF-IgSF interactions involving their N-terminal Ig domains (Barclay, 2003). Extracellular IgSFs represent a biomedically important class of proteins implicated in cancers (Lee et al., 2012; Wai Wong et al., 2012; Xue et al., 2005), infectious (Bergelson et al., 1997; Mendelsohn et al., 1989; White and Littman, 1989), and autoimmune diseases (Bucciarelli et al., 2002; Lebar et al., 1986; Sharpe and Freeman, 2002). They are also proven targets and therapeutic constructs for immunosuppressive drugs (Mansh, 2011; Weber, 2007) and cancer therapies (Watanabe et al., 2005). The importance of extracellular IgSFs is well-documented in immune regulation, where trans-cellular IgSF receptor ligand interactions initiate the molecular cascade that culminates in the destruction of foreign pathogens and malignancies, as well as regulate the tolerance mechanisms that protect the host from harmful autoimmune responses (Lenschow et al., 1996; Salomon and Bluestone, 2001).

A systematic understanding of cognate IgSF receptor-ligand relationships, i.e. binding partners and poses, will provide critical insights into the molecular basis of these diseases and help engineer therapeutic strategies to modulate the underlying receptor-ligand interactions, such as high-affinity mutants of cognate ligands (Larsen et al., 2005). Current knowledge of IgSF interactions is limited: our recent survey of the STRING protein-protein interaction database (Szklarczyk et al., 2011) showed that only 106 (25%) of the extracellular IgSFs have known trans-cellular binding partners supported by high-quality, experimental evidence (Yap et al., 2014). Of these, only 16 IgSF:IgSF complexes have their structures solved by X-ray crystallography to provide detailed insights into the binding interfaces. These 16 IgSF:IgSF complexes are formed by 25 types of IgSF proteins, which can be classified into nine functional families, out of 72 that were identified (Rubinstein et al., 2013). While advances in experimental automation have made possible large-scale screening of up to 1000 receptor-ligand interactions in anecdotal cases (Yu et al., 2009), a brute-force screening of all IgSF-IgSF pairs in the extracellular IgSF subproteome (more than a 100,000 unique combinations) remains intractable. Computational screening is necessary to shortlist potential receptor-ligand pairs for experimental verification. Novel receptor-ligand relationships can be inferred from known relationships in (i) homologous sequences (Rubinstein et al., 2013), (ii) orthologous receptor-ligand pairs ('interology' (Arslan et al., 2008)), and (iii) receptor-ligand pairs sharing similar interface features (Tuncbag et al., 2011). Sequence-based methods have been developed to assign IgSF proteins into coarse-(Rubinstein et al., 2013) and fine-grained (Yap et al., 2014) functional families. These classifications allow transferring of known ligand information within a functional family to predict putative receptor-ligand pairs for testing. In practice, however, inference methods are limited by the paucity of known IgSF-IgSF receptor-ligand information.

In contrast, inference-free, structure-based methods can be applied to any IgSF with a known or modeled structure. However, these approaches are faced with a more challenging question: given an IgSF receptor structure, which protein ligand(s) could be potential binding partners amongst the entire extracellular IgSF subproteome? Existing structure-based methods are not suitable for predicting IgSF receptor-ligand interactions. A major class of such methods relates to small-molecule virtual drug screening, where all possible conformations of a candidate ligand are docked onto the target receptor, and an empirical scoring function is used to identify candidates with high affinity (Fradera and Mestres, 2004). Small-molecule methods cannot be directly applied to protein ligands, because the search space (ligand conformations and poses) scales exponentially with ligand size, rendering these methods computationally intractable for a protein ligand. Another class of structure-based methods is based on protein-protein docking methods, which were traditionally developed for predicting binding poses for two proteins that are known to bind (Smith and Sternberg, 2002). These methods are extensively evaluated in the community wide Critical Assessment of Prediction of Interaction (CAPRI) (Janin, 2005).

Attempts to re-purpose protein-protein docking methods to predict potential ligands for a given target are limited by the difficulty of predicting binding affinities accurately (de Vries et al., 2006). A recent community-wide critical assessment demonstrated that, when current state-of-the-art protein-protein docking methods were used to score and distinguish binders from non-binders, no method could consistently identify cognate binders, and the correlation between docking scores and binding affinity was at best weak (Fleishman et al., 2011). The candidate ligand library in our IgSF-specific application poses additional challenges for protein-protein docking methods, since all candidates from the IgSF subproteome share the same fold topology, and docking methods that rely heavily on receptor-ligand shape complementarity would be less effective in discriminating cognate from non-cognate IgSFs.

The present invention addresses the need for a new method and system for identifying cognate protein ligands.

SUMMARY OF THE INVENTION

A method is provided for identifying a cognate ligand molecule for a known biological receptor comprised of amino acid residues, comprising:

determining interaction energy map data for the known biological receptor, wherein the interaction energy data are determined for the known biological receptor with one or more predefined molecular entities;
determining residue-specific pharmacophore data for the activity of the known biological receptor;
generating ligand spatial interface structure data for the known biological receptor from combining the interaction energy map data and the pharmacophore data;
and screening a candidate ligand molecule for binding to the generated ligand interface structure, and identifying the candidate ligand molecule as a cognate ligand molecule wherein the candidate ligand molecule binds to the generated ligand interface structure, or identifying the candidate ligand molecule as not being a cognate ligand molecule wherein the candidate ligand molecule does not bind to the generated ligand interface structure.

Also provided is a system for identifying a cognate ligand molecule for a known biological receptor comprised of amino acid residues, comprising:
one or more data processing apparatus;
a graphical user interface; and
a non-transitory computer-readable medium coupled to the one or more data processing apparatus having instructions stored thereon which, when executed by the one or more data processing apparatus, cause the one or more data processing apparatus to perform a method comprising:
determining interaction energy map data for the known biological receptor, wherein the interaction energy data are determined for the known biological receptor with one or more predefined molecular entities;
transmitting the interaction energy map data to a viewer application to cause a corresponding interaction energy map to display in the graphical user interface;
determining residue-specific pharmacophore data for the activity of the known biological receptor;
generating ligand spatial interface structure data for the known biological receptor from combining the interaction energy map data and the pharmacophore data;
transmitting the ligand spatial interface structure data to the viewer application to cause display in the graphical user interface of the ligand interface structure as a visual combination of the displayed residue-specific pharmacophore and the displayed interaction energy map; and
screening a candidate ligand molecule for binding to the generated ligand interface structure, and identifying the candidate ligand molecule as a cognate ligand molecule wherein the candidate ligand molecule binds to the generated ligand interface structure, or identifying the candidate ligand molecule as not being a cognate ligand molecule wherein the candidate ligand molecule does not bind to the generated ligand interface structure.

A non-transitory computer readable medium comprising instructions stored thereon for performing the methods described herein is also provided.

Additional objects of the invention will be apparent from the description which follows.

DETAILED DESCRIPTION OF THE INVENTION

Figures 1A, 1B, 1C, 1D, 1E, 1F:
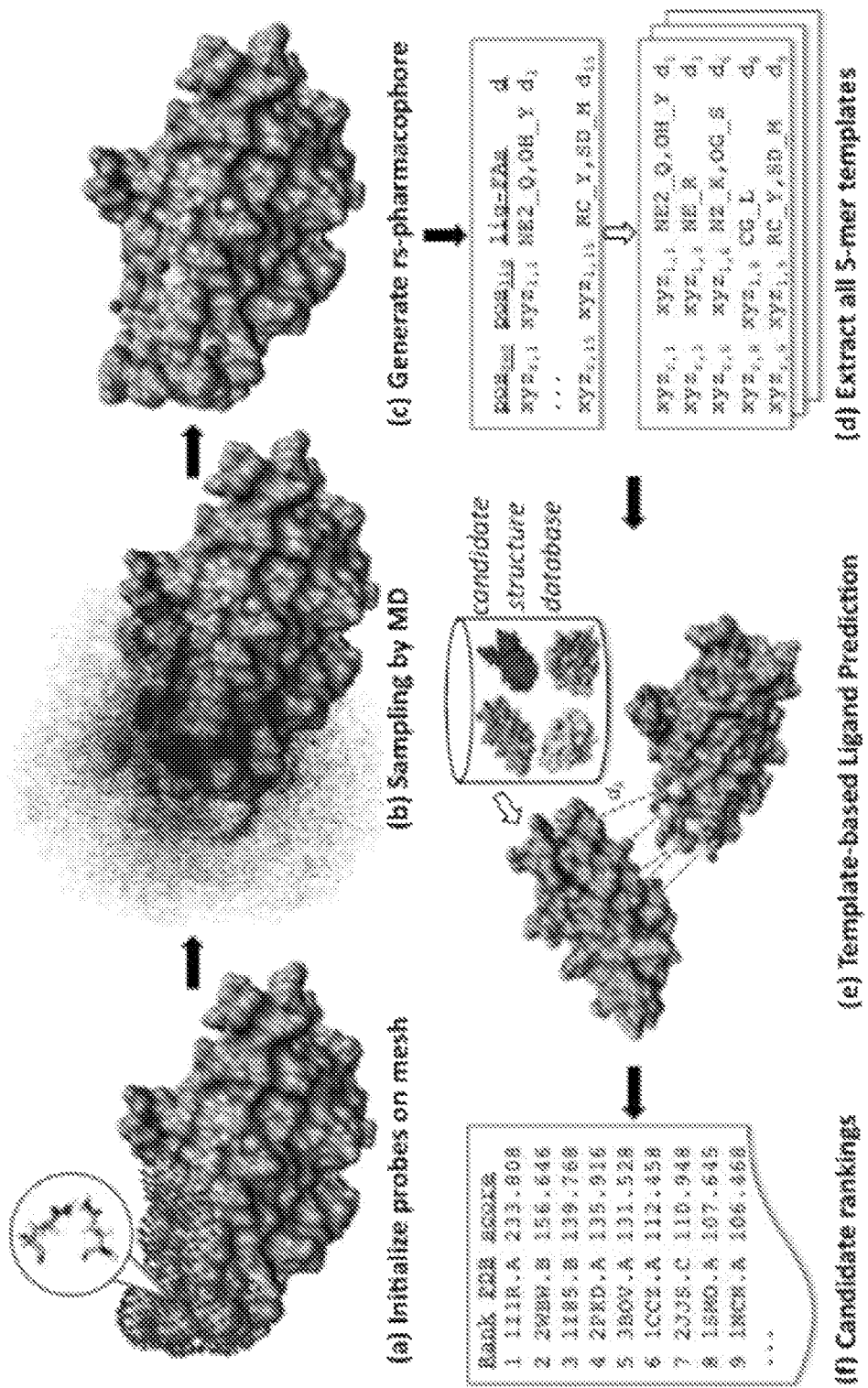
FIG. 1: ProtLID method illustrated using receptor 1I85. D (grey). (a) A 1 Å mesh (red dots) is generated over the receptor interface (orange). Single-residue probes (illustrated here using glutamine) are placed on each mesh point in different orientations. (b) Probes are evolved using MD to collect the positions of the corresponding FA (blue for the NE2 atom of glutamine (NE2_Q)). (c) The spatial distributions of FAs are analyzed to determine the most favored FA types at each receptor site. Three receptor sites favoring NE2_Q are shown in yellow and their corresponding predicted ligand positions in red dots. The actual Gln NE2 position in the bound cognate ligand (green dot) coincides well with the prediction. (d) The resulting rs-pharmacophore comprises predicted ligand position, FA types, and restraint distances for each receptor site. All possible 5-mer templates are generated exhaustively from the full rs-pharmacophore. (e) Each candidate structure in the database is matched against each template: matching 5-atom constellations on the candidate (purple) are least-square-fitted onto predicted ligand positions (red dots). Refinement is then performed to optimize steric clash and distance restraints between ligand (purple) and receptor (yellow) atoms. (f) Qualifying poses are clustered to score and rank all candidate structures. For benchmarking, we monitored the ranks of cognate structures (green entries). See also Table S1.

A method is provided for detecting a cognate ligand molecule for a known biological receptor comprised of amino acid residues, comprising:
determining interaction energy map data for the known biological receptor, wherein the interaction energy data are determined for the known biological receptor with one or more predefined molecular entities;
determining residue-specific pharmacophore data for the activity of the known biological receptor;
generating ligand spatial interface structure data for the known biological receptor from combining the interaction energy map data and the pharmacophore data;
and screening a candidate ligand molecule for binding to the generated receptor interface structure, and detecting the candidate ligand molecule as a cognate ligand molecule wherein the candidate ligand molecule binds to the generated receptor interface structure.

A method is provided for identifying a cognate ligand molecule for a known biological receptor comprised of amino acid residues, comprising:
determining interaction energy map data for the known biological receptor, wherein the interaction energy data are determined for the known biological receptor with one or more predefined molecular entities;
determining residue-specific pharmacophore data for the activity of the known biological receptor;
generating ligand spatial interface structure data for the known biological receptor from combining the interaction energy map data and the pharmacophore data;
and screening a candidate ligand molecule for binding to the generated receptor interface structure, and identifying the candidate ligand molecule as a cognate ligand molecule wherein the candidate ligand molecule binds to the generated receptor interface structure, or identifying the candidate ligand molecule as not being a cognate ligand molecule wherein the candidate ligand molecule does not bind to the generated receptor interface structure.

In an embodiment, the predefined molecular entity is a functional atom of a natural amino acid residue. For example, such as carbon of a methyl group, nitrogen atom of lysine amino group or carboxyl oxygen atom of asparagine. In an embodiment, the predefined molecular entity is a $H_2O$, a methyl group, an amine nitrogen atom, a carboxyl oxygen atom or a hydroxyl.

In an embodiment, the pharmacophore data for the activity of the known biological receptor is determined based on identifying, for amino acid residues of the known biological receptor, one or more of hydrogen bonding, an interactive side chain, a hydrophobic center, an aromatic center, and a charged region of the known biological receptor.

In an embodiment, the residue-specific pharmacophore data is determined by molecular dynamics sampling using single amino acid residue probes.

In an embodiment, the residue-specific pharmacophore data comprise one or more of hydrogen bonding, interactive side chain, hydrophobic and aromatic center data for the receptor.

In an embodiment, the residue-specific pharmacophore is built around the receptor interface based on optimal properties of functional atom types obtained from molecular dynamic sampling.

In an embodiment, the properties of 26 functional atom types are used.

In an embodiment, the properties of 26 functional atom types set forth in Table S1 are used.

In an embodiment, optimal functional atom positions on the receptor interface are determined through sampling of single-residue ligand probes using molecular dynamics. In an embodiment, the method comprises generating a 1 Å-mesh for each receptor interface.

In an embodiment, multiple molecular dynamic trajectories are launched at each mesh point for each single-residue probe type.

In an embodiment, functional atom positions are collected at 1-ps intervals from the trajectories and all functional atom positions that fall within 1 Å of any mesh point are assigned to that mesh point In an embodiment, the known biological receptor is a protein. In an embodiment, the known biological receptor is a human protein. In an embodiment, the known biological receptor is a cell-surface human protein. In an embodiment, the known biological receptor is a secreted human protein. In an embodiment, the candidate ligand molecule is a peptide, a polypeptide or a protein.

In an embodiment, the method further comprises identifying candidate ligand molecules prior to screening them for binding, comprising extracting a template from the residue-specific pharmacophore and matching against a database of experimentally known or computationally modeled ligand structures so as to identify cognate receptor-ligand complexes, and subsequently using candidate ligand molecules corresponding to those identified complementary structures when screening for binding.

In an embodiment, the candidate ligand molecule is a 5-mer amino acid sequence. In an embodiment, determining the residue-specific pharmacophore comprises selecting for residues where hydrogen bond donor-acceptor interactions exist and where hydrophobic contacts exist.

In an embodiment, the method further comprises correcting the generated ligand spatial interface structure data for receptor surface protrusions and indentations.

In an embodiment, the method comprises using the properties of 23 functional atom types. In an embodiment, the method comprises using the properties of the functional atom types set forth in Table S1 except for O_G, N_G and CB_C.

In an embodiment, identifying the candidate ligand molecule as a cognate ligand molecule wherein the candidate ligand molecule binds to the generated receptor interface structure, comprises selecting screened candidate ligand 5-mer molecules which show all inter-atom pairwise distances to be 4 angstroms or less.

Also provided is a system for identifying a cognate ligand molecule for a known biological receptor comprised of amino acid residues, comprising:
one or more data processing apparatus;
a graphical user interface; and
a non-transitory computer-readable medium coupled to the one or more data processing apparatus having instructions stored thereon which, when executed by the one or more data processing apparatus, cause the one or more data processing apparatus to perform a method comprising:
determining interaction energy map data for the known biological receptor, wherein the interaction energy data are determined for the known biological receptor with one or more predefined molecular entities;
transmitting the interaction energy map data to a viewer application to cause a corresponding interaction energy map to display in the graphical user interface;
determining residue-specific pharmacophore data for the activity of the known biological receptor;
generating ligand spatial interface structure data for the known biological receptor from combining the interaction energy map data and the pharmacophore data;
transmitting the ligand spatial interface structure data to the viewer application to cause display in the graphical user interface of the ligand interface structure as a visual combination of the displayed residue-specific pharmacophore and the displayed interaction energy map; and
screening a candidate ligand molecule for binding to the generated receptor interface structure, and identifying the candidate ligand molecule as a cognate ligand molecule wherein the candidate ligand molecule binds to the generated receptor interface structure, or identifying the candidate ligand molecule as not being a cognate ligand molecule wherein the candidate ligand molecule does not bind to the generated receptor interface structure.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, i.e., one or more modules of computer program instructions encoded on a non-transitory computer readable medium for execution by, or to control the operation of, data processing apparatus. The non-transitory computer readable medium can be a machine readable storage device, a machine readable storage substrate, a memory device, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database including a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Non-transitory computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the invention, or any combination of one or more such back-end, middleware, or front-end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

A non-transitory computer readable medium comprising instructions stored thereon for performing the methods described herein is also provided.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

Experimental Details

Currently, computer-based screening methods for identifying cognate protein ligands from libraries are very laborious and require great computational power was well as time. Provided herein is a much improved method which provides efficiencies in all of these limitations. Presented herein is a conceptually new computational approach, Protein Protein Interaction Design (ProtLID) (FIG. 1). ProtLID is inspired by two related concepts in small molecule drug discovery: the molecular interaction field (MIF) (Goodford, 1985) and the pharmacophore (Kier, 1967). A molecular interaction field is a grid-based map reflecting the interaction energetics between a receptor and various generic moieties (e.g. water, methyl group, amine nitrogen, carboxyl oxygen, and hydroxyl). A pharmacophore is an abstract description of key atoms, groups, charged regions, and their spatial interrelations that are essential for a drug molecule's biological activities. Both the MIF and the pharmacophore describe a theoretically optimal ligand interface against which small molecule drug candidates can be screened. To adapt these concepts to a protein ligand we introduce the concept of residue-specific pharmacophoric moieties, herein termed functional atoms (FA). The design is focused on 26 FA types within the 20 naturally occurring amino acid types, specifically, hydrogen-bonding capable side chain oxygen/nitrogen, and hydrophobic/aromatic centers (Table S1) that contribute the most to binding interactions.

TABLE S1

Functional Atom Definitions (related to FIG. 1)

| Interaction Class (i) | Functional Atom (f) | Residue | Atom(s) included | "interactable" receptor atoms |
|---|---|---|---|---|
| Hydrogen bond donor (HB-D) | NE_R | ARG | NE | FAs in HB-A and HB-AD class |
| | NH_RX | ARG | NH1, NH2 | |
| | ND2_N | ASN | ND2 | |
| | NE2_Q | GLN | NE2 | |
| | N_G* | GLY | N | |
| | NZ_K | LYS | NZ | |
| | NE1_W | TRP | NE1 | |
| Hydrogen bond acceptor (HB-A) | OD1_N | ASN | OD1 | FAs in HB-D and HB-AD class |
| | OS_DX | ASP | OD1, OD2 | |
| | OE1_Q | GLN | OE1 | |
| | OS_EX | GLU | OE1, OE2 | |
| | O_G* | GLY | O | |
| | O_P | PRO | O | |
| Hydrogen bond donor and acceptor (HB-AD) | NS_HX | HIS | ND1, NE2 | FAs in HB-A, HB-D, and HB-AD class |
| | OG_S | SER | OG | |
| | OG1_T | THR | OG1 | |
| | OH_Y | TYR | OH | |
| Hydrophobic (HYD) | CB_C* | CYS | CB | sulphur and carbon atom[a] FAs in HYD class[b] |
| | RC_W | TRP | RC | |
| | CG1_I | ILE | CG1 | |
| | CG_L | LEU | CG | |
| | SD_M | MET | SD | |
| | RC_F | PHE | RC | |
| | RC_P | PRO | RC | |
| | RC_Y | TYR | RC | |
| | CG_VX | VAL | CG1, CG2 | |

*functional atom used in reference set (nm), but not for rs-pharmacophore generation
[a]used for snapshot filtering to obtain cf, m
[b]used as receptor-sites for consolidating propensity data The optimal FA positions on the receptor interface are determined through exhaustive sampling of small, single-residue ligand probes using molecular dynamics (MD). The resulting FA preferences constitute a unique spatial fingerprint, herein termed the residue specific (rs) pharmacophore. This designed rs-pharmacophore is then used in the template-based ligand screening step, where we combinatorially extract subtemplates from the rs-pharmacophore and match these designed, theoretical ligand sub-interfaces against candidate structures in the IgSF sub-proteome. The ligand screening step will shortlist the most likely candidates for receptor-ligand interaction and can be used to drastically reduce the number of testable hypotheses for subsequent experimental verification. ProtLID has several conceptual advantages compared to other methods. First, the sampling-derived FA preferences are correlated to free energy, as opposed to empirical scores that are based on a single static snapshot, as in the case of most MIF- and pharmacophore-based methods. This is because FA preferences are quantified by the frequencies that FAs sample each region during all-atom molecular dynamics simulation, which are reflective of the Boltzmann distributions of thermally accessible receptor surface positions. The one other known method that employs MD to generate pharmacophore was pioneered by Mackerell, but with applications for small-molecule and peptide ligands (Guvench and MacKerell, 2009). Second, in contrast to small molecule drug discovery methods, which use generic moieties, ProtLID uses residuespecific moieties, thereby limiting the potential number of matches and reducing the combinatorial search space for screening each candidate protein ligand. Third, the ligand screening step is designed to tolerate variations in crystal structures, through its use of a simple energy function, sub-template matching, and clustering-based ranking scheme. This advantageous feature over both small-molecule and protein-protein docking methods is proven by the consistent rankings of alternative structures of the same candidate protein, a behavior specific to ProtLID. ProtLID was applied to six IgSF receptors belonging to different functional families (Table 1): coxsackievirus and adenovirus receptor (CXAR) binding to CXAR (Protein Data Bank (PDB) code: 1F5 W), cytotoxic T-lymphocyte protein 4 (CTLA-4) binding to CD86 (PDB: 1I85), CTLA-4 binding to CD80 (PDB: 1I8L), CD244 binding to CD48 (PDB: 2PTT), programmed cell death protein 1 (PDCD1) binding to programmed cell death 1 ligand 2 (PD1L2) (PDB: 3BP5), and poliovirus receptor (PVR) binding to TIGIT (PDB: 3UDW). In each case, how well ProtLID ranks structures of the cognate ligands amongst a decoy database of IgSF structures was evaluated. As a comparison, similar rankings were also performed using three state of the art docking algorithms, ClusPro (Comeau et al., 2004a, b; Kozakov et al., 2013; Kozakov et al., 2006), ZDOCK (Pierce et al., 2011), and GRAMM (Katchalskikatzir et al., 1992).

TABLE 1

Six trans-binding, Ig1 interfaces used in ligand prediction.

| Receptor Interface (biological source) | Receptor | | Cognate Ligand | | Interface RMSD [Å] |
|---|---|---|---|---|---|
| | Protein name | Functional Family | Protein name | Structure(s) available | |
| 1F5W.B (h) | CXAR | CXAR | CXAR | 1F5W.A, 2WBW.B, 1EAJ.A, 1KAC.B, 1P6A.B, 2J12.B, 2J1K.A, 2W9L.A | 0.2-2.6 |
| 1I85.D (h) | CTLA4 | CD28/CTLA-4 | CD86 | 1I85.B, 1NCN.A | 1.4 |
| 1I8L.C (h) | CTLA4 | CD28/CTLA-4 | CD80 | 1I8L.A, 1DR9.A | 1.7 |
| 3BP5.A (m) | PDCD1 | Extended CD28/CTLA-4 | PD1L2 | 3BP5.B, 3BOV.A | 1.3-2.4 |
| 2PTT.B (m) | CD244 | SLAM | CD48 | 2PTT.A, 2PTV.A | 1.1 |
| 3UDW.C (h) | PVR | Nectin-like | TIGIT | 3UDW.A, 3Q0H.A, 3RQ3.A, 3UCR.A | 1.0-1.8 |

Receptor interfaces are named by (pdb_id). (receptor-chain), protein names are listed by their UniProt id (source-suffix omitted).
Bound ligand structures are underlined;
biological sources are denoted by 'h' (human) or 'm' (mouse).
Interface RMSD refers to the RMSD of interface residues between bound and unbound forms of the same ligand.

Results

Figure 2:
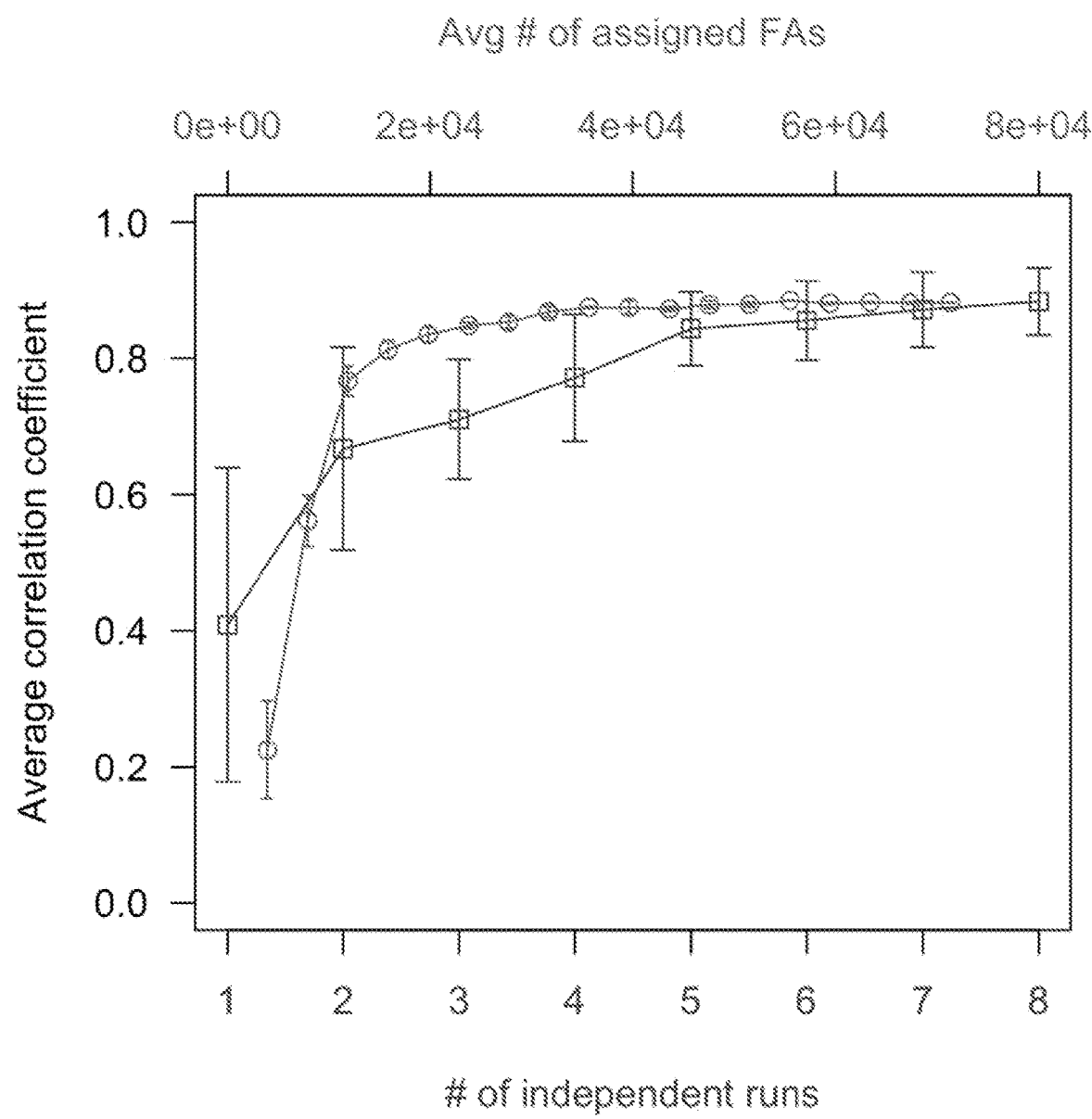
FIG. 2: Average correlation coefficient between pairs of datasets combined from: (red line; upper x-axis) up to 80,000 assigned functional atom positions from 26 functional atom types; or (blue line; lower x-axis) up to 8 runs of a single functional atom type (NE_R).

Exploring criteria for sampling convergence: Molecular dynamic simulations of single-residue ligand probes were performed to determine optimal FA positions. First, a 1 Å-mesh was generated for each receptor interface that resulted in the following numbers of mesh points (Nmesh): 446 (1F5 W.B), 412 (1I85. D), 462 (1I8L. C), 453 (2PTT.B), 583 (3BP5. A), and 427 (3UDW. C). Multiple MD trajectories were launched at each mesh point for each of the 20 single-residue probe types. FA positions were collected at 1-ps intervals from the trajectories and all FA positions that fall within 1 Å of any mesh point were assigned to them. Then nm was determined—the number of FAs assigned to each mesh point m. To establish how many MD runs are required for adequate sampling, two approaches were used to monitor the reproducibility of nm for the receptor 1I85. D (FIG. 2).

In the first approach, two independent datasets were prepared, each comprising ~80,000 assigned FAs from 26 FA types. From each dataset, a gradually increasing total number of assigned FAs (NFA) was randomly selected and nm counted. The random selection was repeated 20 times for each NFA value and the average correlation coefficient of nm against NFA monitored (FIG. 2, red line; upper axis). The plot suggests that at least ~24,000 assigned FAs are needed to have a correlation greater than 0.85. This translates to ~7-8 independent MD runs since each MD run yields on average ~3000 assigned FAs (data not shown).

In a second approach, 16 independent MD runs were performed for the FA type NE_R (NE functional atom of Arg residue). The MD runs were divided into two sets of 8 runs. Next, nruns runs within each set were randomly combined and the correlation coefficient of nm between the two subsets computed. The random combination was repeated 20 times and the average correlation coefficient plotted against nruns (FIG. 2, blue line; lower axis). This result suggests that about six MD runs are sufficient to reproduce a correlation ≥0.85. Guided by the correlation data from both approaches, and to allow for fluctuations in the number of assignable FAs specific to different FA types, it was chosen to perform seven MD runs to ensure sampling convergence.

Generating rs-Pharmacophore: Rs-pharmacophores were generated from the statistical analysis of the MD snapshots. A typical rs-pharmacophore has up to 15 predicted "interactors", each comprising (i) a receptor site (atom type and position), (ii) a corresponding predicted ligand site (allowed FA types and positions), and (iii) a receptor-to ligand atomic distance restraint. The predictive precision of each pharmacophore was benchmarked, which is defined as the ratio of the number of true positive interactors to the total number of interactors. An interactor is considered to be a true positive if there is at least one ligand atom in the bound cognate structure that (i) matches allowed FA types; and (ii) is within the stipulated restraint distance from its receptor site. The precisions of the pharmacophores are 10/15=67% (1F5 W.B), 8/14=57% (1I85. D), 8/15=53% (1I8L. C), 6/15=40% (2PTT.B), 9/15=60% (3BP5. A), and 2/15=13% (3UDW. C). The poor performance of the 3UDW. C predictive precision can be explained by the fact that the native interaction between the receptor PVR with its cognate ligand TIGIT is dominated by main-chain hydrogen bonds: out of the 14 hydrogen bonds between PVR and TIGIT, seven utilize main-chain O or N on the ligand (TIGIT) side (Table S2). Our current approach does not track main-chain N and O, due to their prevalence and lack of specificity.

TABLE S2

Hydrogen bonds between 3UDW.C (PVR) and 3UDW.A (TIGIT) (related to Table 2)

| Receptor (PVR) Atom used | | | Ligand (TIGIT) Atom Used | | |
|---|---|---|---|---|---|
| 63 | GLN | OE1 | 55 | THR | OG1 |
| 73 | GLY | N | 117 | THR | O |
| 127 | THR | O | 56 | GLN | NE2 |
| 132 | SER | OG | 111 | HIS | NE2 |
| 74 | SER | OG | 115 | ASP | O |
| 62 | SER | OG | 56 | GLN | OE1 |
| 62 | SER | OG | 70 | ASN | OD1 |
| 63 | GLN | NE2 | 112 | THR | O |
| 63 | GLN | OE1 | 113 | TYK | N |
| 73 | GLY | O | 117 | THR | N |
| 74 | SER | N | 115 | ASP | O |
| 74 | SER | OG | 114 | PRO | O |
| 82 | GLN | O | 113 | TYR | OH |
| 132 | SER | OG | 58 | ASN | ND2 |

Bold: Hydrogen bonds in which TIGIT uses a main-chain N or O

Ligand prediction results: For each of the six IgSF receptors, we searched its designed rspharmacophores against a candidate database (sub-proteome) of IgSFs represented by their N-terminal Ig (Ig1) domain structures. All available structures of the cognate ligands (Table 1) were also included in the database. The candidates were ranked by ProtLID according to the scoring scheme described in Methods. Table 2 reports the percentile ranks of each cognate structure, in addition to the ranking results obtained using ClusPro, ZDOCK, and GRAMM.

TABLE 2

Cognate ligand prediction results for six IgSF receptors using Cluspro, ZDOCK, GRAMM and ProtLID.

| | Percentile-rank of cognate ligand structures | | | |
|---|---|---|---|---|
| Receptor | Cluspro | ZDOCK | GRAMM | ProtLID |
| 1F5W.B | 100, 100, 67, 52, 98, 90, 77, 83 | 14, 7, 45, 35, 62, 60, 36, 90 | 35, 28, 99, 45, 9, 86, 45, 56 | 2, 1, 5, 3, 8, 16, 9, 7 |
| 1I85.D | 17, 11 (45, 54)$^a$ | 8, 61 (16, 18)$^a$ | 42, 84 (66, 46)$^a$ | 4, 11 (40, 24)$^a$ |
| 1I8L.C | 23, 36 (5, 93)$^b$ | 19, 11 (41, 55)$^b$ | 81, 20 (57, 54)$^b$ | 9, 16 (10, 4)$^b$ |
| 2PTT.B | 56, 9 | 54, 52 | 85, 11 | 8, 9 |

TABLE 2-continued

Cognate ligand prediction results for six IgSF receptors
using Cluspro, ZDOCK, GRAMM and ProtLID.

Percentile-rank of cognate ligand structures

| Receptor | Cluspro | ZDOCK | GRAMM | ProtLID |
|---|---|---|---|---|
| 3BP5.A | 2, 46, 28 | 1, 20, 7 | <u>16</u>, 11, 34 | <u>12</u>, 22, 49 |
| 3UDW.C | 89, 93, 49, 67 | 1, 74, 31, 64 | <u>29</u>, 95, 54, 78 | <u>82</u>, 83, 71, 46 |
| Total # of top 10% ranked ligands | 2/21 | 5/21 | 1/21 | 11/21 |

Percentile ranks are listed in the order of corresponding cognate ligand structures in Table 1.
Underlined: percentile rank of bound cognate structures;
bold: percentile ranks less than or equal to 10.
[a] percentile ranks of cognate structures (1I8L.A, 1DR9.A) for cross-ligand CD80
[b] percentile ranks of cognate structures (1I85.B, 1NCN.A) for cross-ligand CD86

The success of a cognate ligand prediction method can be measured by how often it ranks a cognate ligand better than random, or, more practically, by how often it ranks a cognate ligand at the top, so it could potentially be shortlisted and experimentally verified. For the latter criterion a cutoff value of 10% was chosen, which yields an experimentally tractable number of testable candidates (Table S5). Table 2 summarizes the number of cognate structures ranked within the top 10%. Out of 21 cognate structures, Cluspro, ZDOCK, GRAMM and ProtLID ranked two, five, one, and 11 cognate structures in the top 10%, respectively. The performance is similar if a more stringent test is considered, when the bound cognate ligand structures (underlined in Table 2) were omitted from the list of candidates, since these would not be available in a practical setting when searching for unknown binding partners. Out of a total of 15 known unbound cognate ligand structures, Cluspro, ZDOCK, GRAMM, and ProtLID ranked one, two, one, and seven in the top 10%, respectively.

TABLE S5

Ligand prediction by ProtLID. List of top scoring predicted IgSF
ligands (second column) for the six receptor studied (first column). Ligands are listed in the
order of the best rankings of their corresponding structures. Receptor and ligand structures
are listed by their full name or gene name and in brackets by their corresponding PDB codes,
including chain identification.

| Receptor IgSF | Top 10% ranked Ligand IgSFs (and corresponding structures) |
|---|---|
| CXAR (1F5W.B) | 1. CXAR (1EAJ.A, 1F5W.A, 1P6A.B, 1KAC.B, 2WBW.B, 2JI2.8, 2W9L.A) |
| | 2. Leukocyte-associated immunoglobulin-like receptor 1 (3KGR.A) |
| CTLA4 (1I85.B) | 1. Interleukin-6 receptor subunit beta (1I1R.A) |
| | 2. CXAR (2WBW.B) |
| | 3. CD86 (1I85.B, 1NCN.A) |
| | 4. SLAM family member 5 (2PKD.A) |
| | 5. Programmed cell death 1 ligand 2 (3BOV.A) |
| | 6. Lymphocyte function-associated antigen 3 (1CCZ.A) |
| | 7. Tyrosine-protein phosphatase non-receptor type substrate 1 (2JJS.C) |
| CTLA4 (1I8L.A) | 1. Natural cytotoxicity triggering receptor 1 (1P6F.A) |
| | 2. Advanced glycosylation end product-specific receptor (3O3U.N) |
| | 3. Mucosal addressin cell adhesion molecule 1 (1GSM.A) |
| | 4. CD28 (1YJD.C) |
| | 5. Carcinoembryonic antigen-related cell adhesion molecule 5 (2QST.A) |
| | 6. CD80 (1I8L.A) |
| | 7. Leukocyte-associated immunoglobulin-like receptor 1 (3KGR.A) |
| | 8. Triggering receptor expressed on myeloid cells 1 (1SMO.A) |
| CD244 (2PTT.B) | 1. Advanced glycosylation end product-specific receptor (3O3U.N) |
| | 2. V-set and immunoglobulin domain-containing protein 4 (2ICC.A) |
| | 3. CMRF35-like molecule 1 (1ZOX.A) |
| | 4. Tyrosine-protein phosphatase non-receptor type substrate 1 (2JJS.C) |
| | 5. CD48 (2PTV.A, 2PTT.A) |
| | 6. Neurofascin (3P3Y.A) |
| | 7. Sialoadhesin (1OD9.A) |
| PDCD1 (3BP5.A) | 1. Hepatitis A virus cellular receptor 2 homolog/TIM-3 (3KAA.A) |
| | 2. CD28 (1YJD.C) |
| | 3. Triggering receptor expressed on myeloid cells 1 (1SMO.A) |
| | 4. Intercellular adhesion molecule S (3BN3.B) |
| | 5. Carcinoembryonic antigen-related cell adhesion molecule 5 (2QST.A) |
| | 6. Intercellular adhesion molecule 3 (1TOP.B) |
| | 7. Advanced glycosylation end product-specific receptor (3O3U.N) |
| | 8. Low affinity immunoglobulin gamma Fc region receptor II-a (3D5O.F) |

TABLE S5-continued

Ligand prediction by ProtLID. List of top scoring predicted IgSF
ligands (second column) for the six receptor studied (first column). Ligands are listed in the
order of the best rankings of their corresponding structures. Receptor and ligand structures
are listed by their full name or gene name and in brackets by their corresponding PDB codes,
including chain identification.

| Receptor IgSF | Top 10% ranked Ligand IgSFs (and corresponding structures) |
|---|---|
| PVR (3UDW.C) | 1. CD28 (1YJD.C) |
| | 2. Junctional adhesion molecule-like (3MJ6.A) |
| | 3. Mucosal addressin cell adhesion molecule 1 (1GSM.A) |
| | 4. Lymphocyte function-associated antigen 3 (1CCZ.A) |
| | 5. Intercellular adhesion molecule 2 (1ZXQ.A) |
| | 6. Interleukin-6 receptor subunit alpha (1N26.A) |
| | 7. Immunoglobulin iota chain (2H32.A) |
| | 8. Myelin-oligodendrocyte glycoprotein (1PY9.A) |

Figure 3:
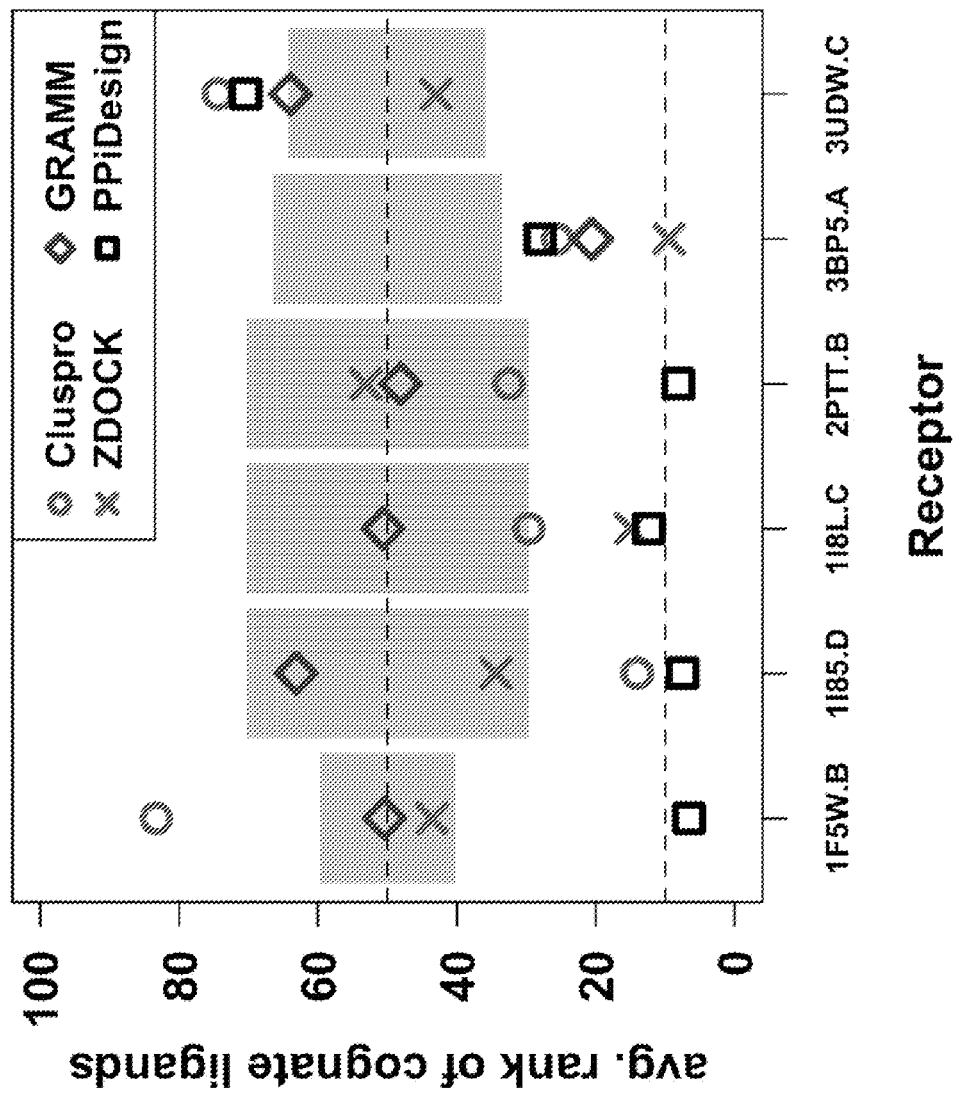
FIG. 3: Performance of ProtLID vs. three docking approaches on six IgSF receptors (x-axis). Insignificant (random) ranking is 50-percentile, with estimated standard deviation shown in grey.

Next assessed were the performances using the average percentile rank of a receptor's cognate structures (FIG. 3 and Table S3). The motivation for this metric is that a high-quality ligand prediction method must be able to perform well with any cognate structure available in the Protein Data Bank. Different structures of the same cognate ligand protein can have significant structural differences and the interface root-mean-squared distance (RMSD) between bound and unbound structures can be as large as 2.6 Å (Table 1). FIG. 3 shows the average percentile rank of cognate ligands for the four methods, with the shaded area representing random performance. ProtLID, on average, ranks cognate ligands better (lower) than random in five out of the six receptors. In contrast, ZDOCK, Cluspro, and GRAMM have two, three and one receptor(s) with average rank better than random, respectively.

TABLE S3

Average percentile ranks of cognate ligand structures
(related to Table 2 and FIG. 3)

| Receptor | Random | Cluspro | ZDOCK | GRAMM | ProtLID |
|---|---|---|---|---|---|
| 1F5W.B | 50.0 ± 9.7 | 83.3 ± 16.0 | 43.6 ± 25.2 | 50.4 ± 27.7 | 6.5 ± 4.5 |
| 1I85.D | 50.0 ± 20.3 | 14.0 ± 3.0 | 34.4 ± 26.9 | 63.1 ± 20.6 | 7.5 ± 3.8 |
| 1I8L.C | 50.0 ± 20.3 | 29.6 ± 6.2 | 15.0 ± 3.8 | 50.6 ± 30.6 | 12.3 ± 3.7 |
| 2PTT.B | 50.0 ± 20.3 | 32.5 ± 23.8 | 53.1 ± 0.6 | 48.1 ± 36.9 | 8.1 ± 0.6 |
| 3BP5.A | 50.0 ± 16.5 | 25.5 ± 17.8 | 9.5 ± 7.7 | 20.6 ± 10.1 | 28.0 ± 15.7 |
| 3UDW.C | 50.0 ± 14.2 | 74.4 ± 17.7 | 43.0 ± 28.8 | 64.0 ± 24.9 | 70.4 ± 14.7 |

Bold: "successful cases", where at least one cognate structure was ranked within the top 10th-percentile.

Another aspect of the performance is the consistency (size of standard deviation) of cognate ligand rankings. If one considers the successful predictions, i.e. cases with at least one cognate structure in the top 10% (bold entries in Table S3), then it is clear that the cognate rankings for ProtLID have small standard deviations (in the range of 0.6-4.5), indicating that it ranked all alternative structures of the same cognate ligand very similarly. In contrast, successful predictions of other methods have large standard deviations (Cluspro: 23.8, 17.8, ZDOCK: 25.2, 26.9, 7.7, 28.8, GRAMM: 27.7), indicating that while some cognate structures were ranked within the top 10%, other alternative structures of the same protein have very disparate ranks. The consistent performance of ProtLID indicates that it is tolerant to differences in crystal structures of the same protein.

Ligand specificity: case study with CTLA-4 binding two different B7s

How well a ligand prediction method based on a particular receptor:ligand interface can recognize a "cross-ligand", i.e. a ligand that binds to the receptor at a similar but not identical interface is of interest. All four ligand prediction methods utilize information about the receptor interface: Cluspro directs docking towards the interface through an attractive potential; ZDOCK and GRAMM poses were filtered to retain only those overlapping with the receptor interface; and ProtLID uses the receptor interface to build its rs-pharmacophore, which in turn guides the docking and selection of matching poses.

The 1I85. D and 1I8L. C receptor interfaces were used to investigate cross ligand specificity. As detailed in Table 1, the 1I85. D interface is derived from a complex of CTLA-4 (1I85, chain D) binding to its ligand CD86 (1I85, chain B), while the 1I8L. C interface is derived from a complex of CTLA-4 (1I8L, chain C) binding to its other ligand CD80 (1I8L, chain A). Both CD86 and CD80 are IgSFs in the B7 functional family, sharing ~25% sequence similarity (Yap et al., 2014).

Figures 4A, 4B:
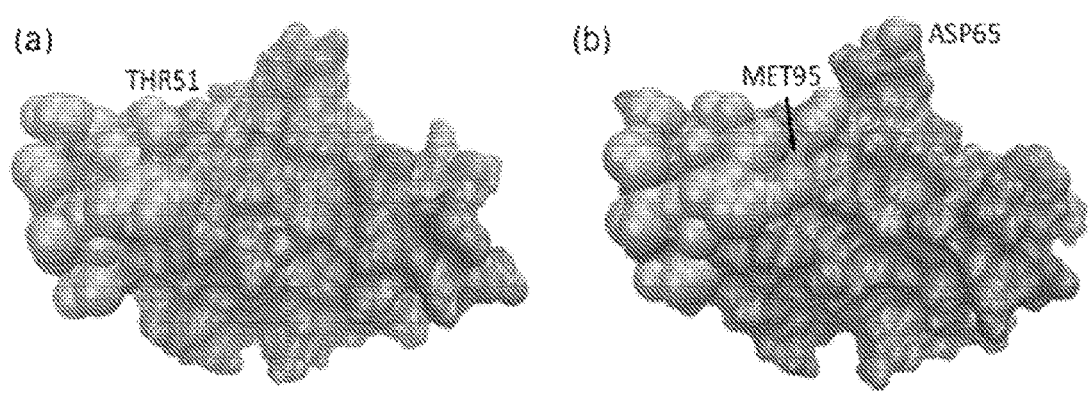
FIG. 4: CTLA-4 binding interfaces for (a) CD86 (PDB code: 1I85) and (b) CD 80 (PDB code: 1I8L). Orange: residues common to both interfaces; magenta and green: residues unique to CD86 and CD80 binding interface, respectively.

While both bind to costimulatory receptors CD28 and CTLA-4, the binding affinities of CD86 are ~5-10 fold lower than that of CD80 (Bhatia et al., 2006). Although the CD80 and CD86 binding sites on CTLA-4 overlap significantly with eight common residues, they are not identical (FIG. 4). CD80 has two unique interface residues (Asp65 and Met97), while CD86 has one (Thr53).

Structures of cross-ligands were added to the respective candidate databases for 1I85. D and 1I8L. C, and their percentile ranks computed (Table 2, entries marked a and b). For the 1I85. D (CD86-binding) interface, none of the methods identified its cross-ligand (CD80; with two available structures 1I8L. A and 1DR9. A) within the top 10%. However, for the 1I8L. C (CD80-binding) interface, two methods successfully identified its cross-ligand, CD86: Cluspro ranked one of the two available structures, 1I85.B, at the top 5%, while ProtLID ranked both structures (1I85.B and 1NCN. A) at top 10% and top 4%, respectively.

It was explored why ProtLID could successfully predict the cross-ligand with the 1I8L. C interface but not with 1I85. D. The poorer ranking of CD80 structures is primarily due to the absence of Asp65 from the interface definition of 1I85. D (FIG. 4). Asp65 is critical for CTLA-4 binding to CD80: forming a salt bridge with Lys89 of CD80 (Henrick, 2007). The absence of Asp65 from the rs-pharmacophore means that a significant subset of specific interactions cannot be considered when searching for a cognate ligand, leading to poorer ranking. ProtLID ranked an alternative ligand for 3UDW. C in top 20%

In the case of 3UDW. C (PVR), Cluspro, GRAMM and ProtLID did not recover any structure of its cognate ligand (TIGIT) within the top 10%. This was expected in case of ProtLID since the rs-pharmacophore of 3UDW. C had a low predictive precision (13%), which is probably a consequence of our choice during method design to omit main-chain N and O from the functional atom definitions, due to their prevalence and lack of specificity. However, analysis of the TIGIT:PVR interface shows that TIGIT uses extensively main chain N and O to interact with PVR (see Table S2). Interestingly, ProtLID did manage to rank another IgSF candidate known to interact with PVR within the top 20%. PVR and TIGIT belong to the nectin/nectin-like IgSF family, whose members are frequently involved in homophilic or heterophilic binding with other family members. Besides TIGIT, PVR is also reported to have binding interactions with other nectin/nectin-like family members: CD226 (Bottino et al., 2003), CD96 (Fuchs et al., 2004), nectin-1 (Harrison et al., 2012), and nectin-3 (Mueller and Wimmer, 2003). Of these, only nectin-1 has a high-resolution structure available (3ALP. A) and was part of the candidate database. ProtLID ranked 3ALP. A at 19.5%. The ranks for 3ALP. A using Cluspro, ZDOCK, and GRAMM are 75.2%, 20.7%, and 87.8%, respectively. ProtLID, ZDOCK reliably rank native-like binding poses as top-scorers Two critical bottlenecks in successfully predicting cognate ligands are the adequate sampling of native-like poses and the subsequent accurate scoring of these poses. A "native-like" was defined pose by two criteria: (i) a more stringent criterion that requires the RMSD of interface residues (RMSDint) between the bound structure and the pose be ≤5 Å, and (ii) a more relaxed criterion that requires 50% of interface residues on the bound structure be also found on the pose's interface. For each criterion, the number of cognate structures was counted for which a method (a) samples at least one native-like pose, and (b) ranks a native-like pose as the top-scoring pose (Table 3).

TABLE 3

| Sampling of native-like poses | | | | |
|---|---|---|---|---|
| Metric | Cluspro | ZDOCK | GRAMM | ProtLID |
| i) Native-like = $RMSC_{int}$ ≤5A | | | | |
| a) # of cognates that sampled native-like pose(s) | 15/21 | 7/21 | 15/21 | 18/21 |
| b) # of cognates whose top-scoring pose is native-like | 4/21 | 0/21 | 7/21 | 11/21 |
| ii) Native-like = share ≥50-percentile of native ligand interface residues | | | | |
| a) # of cognates that sampled native-like pose(s) | 21/21 | 21/21 | 20/21 | 21/21 |

TABLE 3-continued

| Sampling of native-like poses | | | | |
|---|---|---|---|---|
| Metric | Cluspro | ZDOCK | GRAMM | ProtLID |
| b) # of cognates whose top-scoring pose is native-like | 10/21 | 4/21 | 17/21 | 15/21 |

According to the more stringent RMSDint criterion, Cluspro, ZDOCK, and ProtLID sampled native like poses for most cognate structures (15 for Cluspro and ZDOCK, 18 for ProtLID, out of 21 cognate structures), whereas GRAMM (7) was much less efficient in doing so (Table 3 i-a). When ranks were also considered, ProtLID had 11 top scoring cognate ligand structures with native poses, significantly more than Cluspro (4), ZDOCK (0), and GRAMM (7) (Table 3 i-b). Using the second, more relaxed native-like criterion, it appears that all methods are able to reliably sample native poses whose interface coincides at least 50% with the true ligand interface (Table 3 ii-a). However, among these, only ZDOCK and ProtLID are able to rank native-like poses as top-scorers consistently (Table 3 ii-b; 17 for ZDOCK and 15 for ProtLID). The additional hits found in the relaxed criterion (Table 3 ii-b), in comparison with the stringent criterion (Table 3 i-b), suggests that the poses sometimes predict the correct binding patch, albeit in an incorrect orientation. The strong performances of ZDOCK and ProtLID suggest that a potential side application for these methods could be to identify the likely ligand binding interface to improve docking performance (Huang and Schroeder, 2008).

DISCUSSION

Disclosed herein is a new computational approach, ProtLID that predicts the cognate protein ligand for a receptor by matching a residue-specific pharmacophore that reflects functional atom propensities obtained from extensive molecular dynamics sampling around the receptor interface. The method was tested on six known IgSF-IgSF receptor-ligand pairs from functionally diverse IgSF families, and its performance compared against ligand predictions using leading docking algorithms.

This conceptually new approach appears to have several practical advantages over docking methods. First, ProtLID ranked the highest fraction of unbound cognate ligand structures (47%, or seven out of 15) within the top 10%. In contrast, the three other docking-based methods were less sensitive, ranking only 7-13% (1-2 out of 15) of the unbound cognate structures within top 10%.

Second, alternative structures of cognate ligands are ranked consistently by ProtLID, as it is illustrated by the small standard deviation of their rankings. This is important because it highlights the fact that ProtLID's performance is consistent, irrespective of structural variations that exist between similar proteins or for different structures of the same protein when solved under different experimental conditions (Sali, 2001).

A notable failure of identifying the cognate ligand for receptor 3UDW. C was explained by the fact that TIGIT, the cognate ligand of 3UDW. C, uses mainchain contacts in 50% of its hydrogen bond interactions with 3UDW. C. In the current implementation of ProtLID, interactions involving main-chain N and O atoms are ignored due to the ubiquity and non-specificity of such interactions. The only other ligand that ProtLID did not rank in the top 10% is for 3BP5. A, which had a qualitatively good rs-pharmacophore design with a favorable precision of 60%, but it ranked the cognate only in the top 12%, just below our subjective cutoff in this study.

These results suggest that the concept implemented in ProtLID is a suitable tool for shortlisting cognate ligands from sub-proteomes for a given target receptor for verification (Table S5). By employing a computational approach to shortlist ligand candidates one can transform an experimentally unfeasible question to a practical exploration. For instance instead of exploring 5000 interactions in a subproteome of 100 proteins, after shortlisting it drops to only 500 testable cases. Although it is still a very large number of cases to test, at least one recent study successfully explored nearly a 1000 receptor-ligand interactions (Yu et al., 2009). The computationally intensive step in the current implementation of ProtLID is the molecular dynamics sampling of FA propensities to design the rspharmacophore. However, the cost is justified by the more accurate and consistent performance attained in comparison to state-of-the-art docking algorithms. Once an rs-pharmacophore is built, it can be used to search quickly against any large set of candidates in a parallel computational fashion. This makes the current method a good candidate to explore protein interactions within a variety of subproteomes or the entire set of structurally known proteins.

Methods

The following datasets used in this study:

(A) List of Extracellular IgSFs—The set of extracellular human IgSF proteins was obtained as in (Rubinstein et al., 2013). Briefly, human IgSF proteins were identified from the UniProt database (Apweiler et al., 2010), if they are predicted to be membrane-integral or secreted by the Phobius program (Kali et al., 2004), and their InterPro identifiers correspond to Ig domains. Antibodies and T-cell receptors were excluded, and the highly polymorphic MHC I/II proteins were represented by only one protein per gene. This resulted in an IgSF dataset with 477 proteins (Supplementary Table 1 of (Yap et al., 2014)), of which a subset of 366 has an N-terminal Ig domain (Ig1 set).

(B) Trans-binding IgSF-IgSF interfaces—a list of 39 known trans-binding, heterophillic IgSF-IgSF pairs was compiled (Yap et al., 2014) and seven trans-binding, homophillic IgSF-IgSF pairs (Cao et al., 2006; Dong et al., 2006; Harrison et al., 2012; Patzke et al., 2010; Rubinstein et al., 2013; Yan et al., 2007). For each of these IgSF-IgSF pairs, we queried the UniProt database for complex structures with resolution ≤3.5 Å, and coverage ≥90% for both receptor and ligand chains. Complexes that (i) involved mixed species, (ii) did not interact in a trans-binding orientation, (iii) interfaces involved regions other than the Ig1 domain were omitted. Sixteen X-ray structures of transbinding human or mouse IgSF-IgSF were found that contain a total of 25 unique IgSF interfaces belonging to nine functional families. Six receptor interfaces from the largest families were selected for the current study (Table 1).

(C) Candidate structure database—the UniProt database was queried for X-ray structures (resolution ≤3.0 Å, coverage ≥90%) for the 366 extracellular IgSFs in the Ig1 set. When no structure of the human protein was found, we collected available structures from mouse and rat homologs. A total of 79 Ig1 structures were found (Table S4), comprising 62 human, 15 mouse, and 2 rat structures. The performance of ProtLID for mouse and rat structures were comparable to human structures, indicating no intrinsic bias against non-human sources. For each receptor, the candidate database was supplemented with all available structures of its cognate ligand (resolution ≤3.5 Å, coverage ≥90%, where the source must be the same species as the receptor protein). Structures with mutations were excluded. The list of cognate PDBs are provided in Table 1.

TABLE S4

Primary candidate database with 79 Ig1 protein structures (related to Table 1).

| IgSF | PDB_id. chain_id | Res. [Å] | Residue range | Source |
| --- | --- | --- | --- | --- |
| BCAM | 2PF6.A | 2.20 | 32-144 | human |
| BTLA | 2AW2.A | 2.80 | 34-137 | human |
| CADM2 | 3M45.A | 2.21 | 26-124 | mouse |
| CADM3 | 1Z9M.A | 2.40 | 28-132 | human |
| CD2 | 1HNF.A | 2.50 | 28-127 | human |
| CD244 | 2PTT.B | 1.63 | 21-128 | mouse |
| CD28 | 1YJD.C | 2.70 | 19-136 | human |
| CD3E | 1XIW.A | 1.90 | 33-123 | human |
| CD4 | 3O2D.A | 2.19 | 26-123 | human |
| CD47 | 2JJS.C | 1.85 | 2-116 | human |
| CD48 | 2PTT.A | 1.63 | 27-128 | mouse |
| CD86 | 1NCN.A | 2.70 | 26-134 | human |
| CD8A | 2HP4.A | 2.10 | 22-135 | human |
| CD8B | 3DMM.D | 2.60 | 22-144 | mouse |
| CEAM1 | 2GK2.A | 2.20 | 34-141 | human |
| CEAM5 | 2QST.A | 2.96 | 34-144 | human |
| CLM1 | 1ZOX.A | 2.10 | 20-128 | mouse |
| CLM6 | 2Q87.A | 1.70 | 19-125 | human |
| CRTAM | 9CRT.A | 2.32 | 19-116 | human |
| CSF3R | 2D9Q.B | 2.80 | 26-120 | human |
| CTLA4 | 3OSK.A | 1.80 | 38-158 | human |
| CXAR | 2WBW.B | 1.55 | 19-138 | human |
| FCG2A | 3DSO.F | 2.80 | 37-122 | human |
| FCG2B | 2FCB.A | 1.74 | 46-130 | human |
| FCG3B | 1FNL.A | 1.80 | 21-107 | human |
| GPV1 | 2GI7.A | 2.40 | 22-107 | human |
| ICAM1 | 1LAM.A | 2.10 | 28-110 | human |
| ICAM2 | 1ZXQ.A | 2.20 | 25-109 | human |
| ICAM3 | 1T0P.B | 1.66 | 30-114 | human |
| ICAM5 | 3BN3.B | 2.10 | 32-117 | human |
| IGLL1 | 2H3N.B | 2.30 | 94-209 | human |
| IL12B | 3DUH.A | 2.30 | 23-113 | human |
| IL1R1 | 1ITB.B | 2.50 | 23-114 | human |
| IL6RA | 1N26.A | 2.40 | 20-111 | human |
| IL6RB | 1I1R.A | 2.40 | 24-123 | human |
| JAM1 | 1NBQ.A | 2.90 | 27-130 | human |
| JAML1 | 3MJ6.A | 2.19 | 30-141 | mouse |
| KI2L1 | 1NKR.A | 1.70 | 27-124 | human |
| KI2L2 | 2DLL.A | 2.90 | 26-123 | human |
| KI2S2 | 1M4K.A | 2.30 | 29-123 | human |
| KIT | 2O26.U | 2.50 | 36-114 | mouse |
| LAIR1 | 3KGR.A | 1.80 | 25-122 | human |
| LFA3 | 1CCZ.A | 1.80 | 29-121 | human |
| LIRB1 | 3D2U.D | 2.21 | 26-119 | human |
| LIRB2 | 2DYP.D | 2.50 | 26-119 | human |
| MADCA | 1GSM.A | 1.90 | 23-112 | human |
| MOG | 1PY9.A | 1.80 | 30-145 | mouse |
| MUSK | 2IEP.A | 2.21 | 24-118 | rat |
| NCAM1 | 1EPF.A | 1.85 | 20-117 | rat |
| NCAM2 | 2XY2.A | 1.77 | 19-112 | human |
| NCTR1 | 1P6F.A | 2.20 | 25-118 | human |
| NCTR2 | 1HKF.A | 2.20 | 23-130 | human |
| NFASC | 3P3Y.A | 2.60 | 37-137 | human |
| OBSL1 | 3KNB.B | 1.40 | 8-103 | human |
| PD1L1 | 3FN3.B | 2.70 | 19-131 | human |
| PD1L2 | 3BOV.A | 1.77 | 20-123 | mouse |
| PDCD1 | 3BIK.B | 2.65 | 33-146 | mouse |
| PGFRB | 3MJG.X | 2.30 | 33-104 | human |
| PIGR | 1XED.E | 1.90 | 20-127 | human |
| PTPRF | 3PXH.A | 2.00 | 30-126 | mouse |
| PVRL1 | 3ALP.A | 2.80 | 36-143 | human |
| RAGE | 3O3U.N | 1.50 | 24-120 | human |
| ROBO1 | 2V9T.A | 1.70 | 61-166 | human |
| SHPS1 | 2UV3.A | 1.80 | 32-148 | human |
| SIGL5 | 2ZG2.A | 2.85 | 20-142 | human |
| SIGL7 | 1O7V.A | 1.90 | 18-144 | human |
| SIRBL | 2JJV.B | 1.80 | 32-148 | human |
| SLAF5 | 2PKD.A | 2.04 | 25-131 | human |
| SN | 1OD9.A | 2.10 | 20-138 | mouse |

TABLE S4-continued

Primary candidate database with 79 Ig1 protein structures (related to Table 1).

| IgSF | PDB_id. chain_id | Res. [Å] | Residue range | Source |
|---|---|---|---|---|
| TIE2 | 2GY5.A | 2.90 | 23-120 | human |
| TIGIT | 3Q0H.A | 1.70 | 22-130 | human |
| TIMD1 | 2OR8.A | 2.50 | 20-130 | mouse |
| TIMD3 | 3KAA.A | 3.00 | 29-131 | mouse |
| TIMD4 | 3BIA.X | 2.20 | 25-134 | mouse |
| TREM1 | 1SMO.A | 1.47 | 21-133 | human |
| TRML1 | 2FRG.P | 1.19 | 20-125 | human |
| VCAM1 | 1VSC.A | 1.90 | 25-114 | human |
| VPREB | 2H32.A | 2.70 | 20-120 | human |
| VSIG4 | 2ICC.A | 1.20 | 19-137 | human |

ProtLID protocol—an overview of the method is shown in FIG. 1.

(A) Probe-based pharmacophore generation Mesh placement over receptor interface: Interface atoms on the receptor were identified from solved complex structures (FIG. 1a), using the CSU program (Sobolev et al., 1999) with the following additional criteria: (i) contact distance ≤4 Å; (ii) contacting atoms are from legitimate CSU classes (Table 1 of (Sobolev et al., 1999)); (iii) solvent accessible surface area per NACCESS (Hubbard and Thornton, 1993) is greater than 1 A2; (iv) carbon or sulfur atoms must come from hydrophobic residues. A 1 Å-mesh was then generated on the solvent-accessible surface of the receptor using the software EDTSurf (Xu and Zhang, 2009) with a probe radius of 1 Å.

Sampling using molecular dynamics Sampling for optimal FA positions (FIG. 1b) was conducted by simulating single residue ligand-probes' on the receptor surface using the AMBER molecular dynamics package (Case et al., 2005). Uncapped (N—H at N-terminal and C═O at C-terminal) ligand-probes were placed on each interface mesh point. The receptor-probe system was minimized for 5000 steps, with harmonic restraints on receptor heavy atoms and ligand functional atoms gradually reduced from 5.0 kcal/mol to zero. Molecular dynamics was performed at T=300 K using Andersen thermal coupling and implicit solvation with no periodic boundary condition. A distance restraint of 15 Å was maintained between the ligand functional atom and the starting mesh point. Each trajectory was evolved for 40 ps, with energy minimized snapshots of the probe collected every 1 ps. Seven independent MD runs were launched from each mesh point by varying the initial orientation of the probe with respect to the receptor.

Rs-pharmacophore generation from MD Snapshots: To generate an rs-pharmacophore (FIG. 1c), MD data collected for 26 FA types were analyzed in several steps. For each FA type f and MD run r, we filtered the snapshots for the presence of legitimate hydrogen bond donor-acceptor interactions or hydrophobic contacts. For each mesh point m, we computed the number of assigned FAs (cf,m), averaged over seven MD runs.

Protrusions and indentations on the receptor surface can lead to under- and over-sampling artifacts. We addressed this problem by normalizing cf,m by its expected value as follows. We computed nm, the FA-independent reference mesh count, by assigning FA positions from all snapshots to the nearest mesh point, averaging the FA counts at each mesh point over seven MD runs and adding a pseudocount of 10 to each mesh point to compensate for low counts. We then used nm to generate cf,m,expected, the "expected" count at mesh point m for a functional atom type f that belongs to the interaction class i:

$$C_{f,m,expected} = \frac{n_m}{\sum_{m \in \{m\_i\}} |n_m|} + \sum_{m \in \{m\_i\}} C_{f,m}$$

where {m_i} is the set of mesh points for which functional atoms of interaction type i are expected to have non-zero counts. The ratio of actual-to-expected assigned FA counts, A/E ratio f,m=c f,m c f,m,expected, represents the propensity distribution of functional atom f at mesh m, after normalizing for surface geometry-based sampling effects.

While the reference distribution used all 26 FA types, three FA types (O_G, N_G, and CB_C) were omitted from the final rs-pharmacophore design: O_G and N_G were not used since main-chain N and O are ubiquitous in all ligand structures and likely to produce spurious matches and extend the search time; CB_C was omitted because solvent-exposed, unpaired cysteines are infrequent in the oxidative extracellular environment (Fiser and Simon, 2002).

Of the remaining 23×Nmesh (f,m)-combinations on the receptor interface, we retained (f,m) with above average propensities (i.e. A/E ratio ≥1) and at least a minimal number of occurrence (cf,m≥2). These were consolidated into "interactors" on the receptor interface, where each interactor comprises (i) a receptor site position, (ii) the predicted ligand position, given by the mesh point closest to the geometric center of all assigned (f,m); (iii) the permitted ligand FA types, given by the FA types found in the top 10% (f,m) when ranked by A/E ratiof,m, (iv) and a stipulated restraint distance between the receptor site and matching ligand atom. The complete set of interactors constitutes the rspharmacophore.

(B) Template-based cognate ligand prediction using rs-pharmacophore Each candidate structure is compared to the N-interactor rs-pharmacophore via NC5 5-interactor templates generated from the full rs-pharmacophore (FIG. 1d). For each template, we exhaustively searched a candidate structure for matching 5-mer atom constellations ("constellation search"), and then refined the resulting poses of the candidate structure. Low energy poses from all templates are clustered, and the number of poses is used as a measure of similarity to the rspharmacophore.

Constellation Search: The constellation search (FIG. 1e) comprised the following steps: (i) for each interactor in the template, all candidate atoms matching its allowed FA types were identified. (ii) From these all 5-mer atom combinations were generated, and those ligand matches where all of the inter-atom pairwise distances were deviating less than 4 Å were retained. (iii) Ligands with matching constellations were least-square fitted onto their corresponding rspharmacophore positions, resulting in the guided docking of the full candidate structure onto the receptor.

Energy Refinement: Docked poses were refined to minimize clashes and optimize distances between the 5 candidate-receptor atom pairs using the following energy function:

$$E = E_{clash} + E_{restraint}$$

-continued $$E_{clash} = \begin{cases} 1000000; & p_{clash} \geq p_{clash,max} \\ 0.5k_{clash}(p_{clash} - p_{clash,max})^2; & p_{clash,min} \leq p_{clash} < p_{clash,max} \\ 0; & p_{clash} < p_{clash,min} \end{cases}$$

$$E_{restraint} = \sum_{k=1}^{5} E_{restraint,k}$$

$$E_{restraint,k} = \begin{cases} 0.5k_{upper}(r_{cut,k} - r)^2; & r > r_{cut,k} \\ 0; & 3.0 \leq r < r_{cut,k} \\ 0.5k_{lower} r^2; & r < 3.0 \end{cases}$$

where pclash is the percentage of receptor heavy atoms that are within 3 Å of any candidate atoms, pclash,min and pclash,max set to 5% and 20% respectively; and kclash=554. The restraint energy is a sum of 5 harmonic distance restraints, with kupper=10.0; klower=222.22, and rcut,k is 4.5-4.7 Å for hydrogen bond receptor sites and 8 Å for hydrophobic receptor sites. Candidate poses with no energy violation (E=0) were kept and clustered at 5 Å RMSD of interface atoms.

Scoring and ranking candidate ligand structures: For each pose, the interface area, Aint=Areceptor+Aligand−Acomplex, was computed using the NACCESS program, and this converted into a normalized score (norm_Aint) between 0 and 1. The score for candidate structure I is then given by the sum of poses in its largest cluster, each weighted by its norm_Aint. The percentile ranking of candidate I is the number of other candidates with equal or better scores, divided by the total number of candidate structures×100 (FIG. 10. Ligand prediction using docking algorithms ClusPro: Each receptor was docked against each candidate structure using the ClusPro server (http://cluspro.bu.edu (Brenke et al., 2012; Comeau et al., 2004a, b; Kozakov et al., 2013; Kozakov et al., 2006)) with three different force fields: antigen:antibody (ab), enzyme:inhibitor (ei), and other (o). For each docking submission the list of core receptor interface residues was provided for which attractive interactions were to be applied. For each force field category, we scored and ranked each candidate based on the number of poses in its biggest cluster. The average rank across three force fields was then used to re-rank the candidates and compute the percentile ranks, similar to ProtLID.

ZDOCK and GRAMM: The partner search procedures for ZDOCK (Pierce et al., 2011) and GRAMM were similar. For each receptor:candidate-structure docking, 500 poses were generated. For GRAMM, the grid step was increased from 1.7 Å (default) to 2.0 Å or 2.5 Å whenever necessary to accommodate the structures within the grid. The poses were post-filtered to retain only those that docked to the receptor interface. Specifically, the receptor interface in the pose (atoms within 4 Å of any candidate atom) must share at least $N_{recIntRes,overlap}$ common residues with the actual receptor interface. Various values of $N_{recIntRes,overlap}$ were explored but there was no systematic trend in performance for ZDOCK and GRAMM. We set $N_{recIntRes,overlap}$=5 to correspond with the 5-interactor template criterion used in ProtLID. The score of a candidate structure was the lowest energy among those of the remaining poses. Percentile ranks were computed as in ProtLID.

Random ranking benchmarks: For each receptor, we sorted structures in its candidate database randomly, and used the resulting ranks of cognate structures to compute the average cognate ranks. Up to 100,000 random trials were performed to ensure that the average and standard deviation converged to stable values.

Native-like Pose Analysis: Poses were analyzed to determine if they are native-like, using two different criteria. For each complex structure, we first obtained the list of true ligand interface residues, as provided by the CSU program and with the additional requirements that all contact distances be ≤4 Å, and that the atom pairs must be legitimate as defined by CSU. The first native-like criterion is based on RMSDint, the RMSD of true ligand interface residues between the bound ligand structure and the ligand pose. A pose with RMSDint ≤5 Å is considered native-like. The second criterion is based on the percentage of shared interface residues. For each pose, we determined its interface residues, defined as residues with at least one atom within 4 Å of any receptor atom. If a pose contained ≥50% of the true ligand interface residues, it was considered native-like. For each partner search method, the number of cognate structures were then counted that (i) sampled any native-like pose, and for which (ii) the top scoring pose was native-like. For ZDOCK and GRAMM, the poses analyzed always satisfied the $N_{recIntRes,overlap}$ requirement (see above). For ClusPro, the reported values are the averages from three force fields.

REFERENCES

1. Apweiler, R., Martin, M. J., O'Donovan, C., Magrane, M., Alam-Faruque, Y., Antunes, R., Barrell, D., Bely, B., Bingley, M., Binns, D., et al. (2010). The Universal Protein Resource (UniProt) in 2010. Nucleic Acids Res 38, D142-D148.
2. Arslan, M., Boyce, M. C., Qi, H. J., and Ortiz, C. (2008). Constitutive modeling of the stress-stretch behavior of two-dimensional triangulated macromolecular networks containing folded domains. J Appl Mech-T Asme 75.
3. Barclay, A. N. (2003). Membrane proteins with immunoglobulin-like domains—a master superfamily of interaction molecules. Semin Immunol 15, 215-223.
4. Bergelson, J. M., Cunningham, J. A., Droguett, G., KurtJones, E. A., Krithivas, A., Hong, J. S., Horwitz, M. S., Crowell, R. L., and Finberg, R. W. (1997). Isolation of a common receptor for coxsackie B viruses and adenoviruses 2 and 5. Science 275, 1320-1323.
5. Bhatia, S., Edidin, M., Almo, S. C., and Nathenson, S. G. (2006). B7-1 and B7-2: Similar costimulatory ligands with different biochemical, oligomeric and signaling properties. Immunol Lett 104, 70-75.
6. Bottino, C., Castriconi, R., Pende, D., Rivera, P., Nanni, M., Carnemolla, B., Cantoni, C., Grassi, J., Marcenaro, S., Reymond, N., et al. (2003). Identification of PVR (CD155) and nectin-2 (CD112) as cell surface ligands for the human DNAM-1 (CD226) activating molecule. J Exp Med 198, 557-567.
7. Brenke, R., Hall, D. R., Chuang, G. Y., Comeau, S. R., Bohnuud, T., Beglov, D., Schueler-Furman, O., Vajda, S., and Kozakov, D. (2012). Application of asymmetric statistical potentials to antibody-protein docking. Bioinformatics 28, 2608-2614.
8. Bucciarelli, L. G., Wendt, T., Rong, L., Lalla, E., Hofmann, M. A., Goova, M. T., Taguchi, A., Yan, S. F., Yan, S. D., Stern, D. M., et al. (2002). RAGE is a multiligand receptor of the immunoglobulin superfamily: implications for homeostasis and chronic disease. Cell Mol Life Sci 59, 1117-1128.

9. Cao, E., Ramagopal, U. A., Fedorov, A., Fedorov, E., Yan, Q. R., Lary, J. W., Cole, J. L., Nathenson, S. G., and Almo, S. C. (2006). NTB-A receptor crystal structure: Insights into homophilic interactions in the signaling lymphocytic activation molecule receptor family. Immunity 25, 559-570.
10. Case, D. A., Cheatham, T. E., Darden, T., Gohlke, H., Luo, R., Merz, K. M., Onufriev, A., Simmerling, C., Wang, B., and Woods, R. J. (2005). The Amber biomolecular simulation programs. J Comput Chem 26, 1668-1688.
11. Comeau, S. R., Gatchell, D. W., Vajda, S., and Camacho, C. J. (2004a). ClusPro: a fully automated algorithm for protein-protein docking. Nucleic Acids Res 32, W96-W99.
12. Comeau, S. R., Gatchell, D. W., Vajda, S., and Camacho, C. J. (2004b). ClusPro: An automated docking and discrimination method for the prediction of protein complexes. Bioinformatics 20, 45-50.
13. de Vries, S. J., van Dijk, A. D. J., and Bonvin, A. M. J. J. (2006). WHISCY: What information does surface conservation yield? Application to data-driven docking. Proteins 63, 479-489.
14. Dong, X. H., Xu, F., Gong, Y. H., Gao, J., Lin, P., Chen, T., Peng, Y., Qiang, B. Q., Yuan, J. G., Peng, X. Z., et al. (2006). Crystal structure of the v domain of human nectin-lik molecule-1/Syncam3/Tsl11/Igsf4b, a neural tissue-specific immunoglobulin-like cell-cell adhesion molecule. J Biol Chem 281, 10610-10617.
15. Fiser, A., and Simon, I. (2002). Predicting redox state of cysteines in proteins. Method Enzymol 353, 10-21.
16. Fleishman, S. J., Whitehead, T. A., Strauch, E. M., Corn, J. E., Qin, S. B., Zhou, H. X., Mitchell, J. C., Demerdash, O. N. A., Takeda-Shitaka, M., Terashi, G., et al. (2011). Community-Wide Assessment of Protein-Interface Modeling Suggests Improvements to Design Methodology. J Mol Biol 414, 289-302.
17. Fradera, X., and Mestres, J. (2004). Guided docking approaches to structure-based design and screening. Curr Top Med Chem 4, 687-700. Fuchs, A., Cella, M., Giurisato, E., Shaw, A. S., and Colonna, M. (2004). Cutting edge: CD96 (Tactile) promotes NK cell-target cell adhesion by interacting with the poliovirus receptor (CD155). J Immunol 172, 3994-3998.
18. Goodford, P. J. (1985). A Computational-Procedure for Determining Energetically Favorable Binding-Sites on Biologically Important Macromolecules. J Med Chem 28, 849-857.
19. Guvench, O., and MacKerell, A. D. (2009). Computational Fragment-Based Binding Site Identification by Ligand Competitive Saturation. Plos Comput Biol 5.
20. Harrison, O. J., Vendome, J., Brasch, J., Jin, X. S., Hong, S., Katsamba, P. S., Ahlsen, G., Troyanovsky, R. B., Troyanovsky, S. M., Honig, B., et al. (2012). Nectin ectodomain structures reveal a canonical adhesive interface. Nat Struct Mol Biol 19, 906-915.
21. Henrick, E. K.a.K. (2007). 'Protein interfaces, surfaces and assemblies' service PISA at the European Bioinformatics Institute (J. Mol. Biol).
22. Huang, B., and Schroeder, M. (2008). Using protein binding site prediction to improve protein docking. Gene 422, 14-21.
23. Hubbard, S. J., and Thornton, J. M. (1993). 'NACCESS', computer program.
24. Janin, J. (2005). Assessing predictions of protein-protein interaction: The CAPRI experiment. Protein Sci 14, 278-283.
25. Kall, L., Krogh, A., and Sonnhammer, E. L. L. (2004). A combined transmembrane topology and signal peptide prediction method. J Mol Biol 338, 1027-1036.
26. Katchalskikatzir, E., Shariv, I., Eisenstein, M., Friesem, A. A., Aflalo, C., and Vakser, I. A. (1992). Molecular-Surface Recognition—Determination of Geometric Fit between Proteins and Their Ligands by Correlation Techniques. P Natl Acad Sci USA 89, 2195-2199.
27. Kier, L. B. (1967). Molecular orbital calculation of preferred conformations of acetylcholine, muscarine, and muscarone. Molecular pharmacology 3, 487-494.
28. Kozakov, D., Beglov, D., Bohnuud, T., Mottarella, S. E., Xia, B., Hall, D. R., and Vajda, S. (2013). How good is automated protein docking? Proteins 81, 2159-2166.
29. Kozakov, D., Brenke, R., Comeau, S. R., and Vajda, S. (2006). PIPER: An FFT-based protein docking program with pairwise potentials. Proteins 65, 392-406.
30. Lander, E. S., Consortium, I. H. G. S., Linton, L. M., Birren, B., Nusbaum, C., Zody, M. C., Baldwin, J., Devon, K., Dewar, K., Doyle, M., et al. (2001). Initial sequencing and analysis of the human genome. Nature 409, 860-921.
31. Larsen, C. P., Pearson, T. C., Adams, A. B., Tso, P., Shirasugi, N., Strobert, E., Anderson, D., Cowan, S., Price, K., Naemura, J., et al. (2005). Rational development of LEA29Y (belatacept), a high-affinity variant of CTLA4-lg with potent immunosuppressive properties. Am J Transplant 5, 443-453.
32. Lebar, R., Lubetzki, C., Vincent, C., Lombrail, P., and Boutry, J. M. (1986). The M2 Autoantigen of Central-Nervous-System Myelin, a Glycoprotein Present in Oligodendrocyte Membrane. Clin Exp Immunol 66, 423-434.
33. Lee, G., Zhu, M. G., Ge, B. X., and Potzold, S. (2012). Widespread expressions of immunoglobulin superfamily proteins in cancer cells. Cancer Immunol Immun 61, 89-99.
34. Lenschow, D. J., Walunas, T. L., and Bluestone, J. A. (1996). CD28/B7 system of T cell costimulation. Annu Rev Immunol 14, 233-258.
35. Mansh, M. (2011). Ipilimumab and cancer immunotherapy: a new hope for advanced stage melanoma. Yale J Biol Med 84, 381-389.
36. Mendelsohn, C. L., Wimmer, E., and Racaniello, V. R. (1989). Cellular Receptor for
37. Poliovirus—Molecular-Cloning, Nucleotide-Sequence, and Expression of a New Member of the Immunoglobulin Superfamily. Cell 56, 855-865.
38. Mueller, S., and Wimmer, E. (2003). Recruitment of nectin-3 to cell-cell junctions through trans-heterophilic interaction with CD155, a vitronectin and poliovirus receptor that localizes to alpha(v)beta(3) integrin-containing membrane microdomains. J Biol Chem 278, 31251-31260.
39. Patzke, C., Max, K. E. A., Behlke, J., Schreiber, J., Schmidt, H., Dorner, A. A., Kroger, S., Henning, M., Otto, A., Heinemann, U., et al. (2010). The Coxsackievirus-Adenovirus Receptor Reveals Complex Homophilic and Heterophilic Interactions on Neural Cells. J Neurosci 30, 2897-2910.
40. Pierce, B. G., Hourai, Y., and Weng, Z. P. (2011). Accelerating Protein Docking in ZDOCK Using an Advanced 3D Convolution Library. Plos One 6.
41. Rubinstein, R., Ramagopal, U. A., Nathenson, S. G., Almo, S. C., and Fiser, A. (2013). Functional Classification of Immune Regulatory Proteins. Structure 21, 766-776.

42. Sali, A. (2001). Comparative protein structure modeling of genes and genomes. Abstr Pap Am Chem S 222, U390-U390.
43. Salomon, B., and Bluestone, J. A. (2001). Complexities of CD28/B7: CTLA-4 costimulatory pathways in autoimmunity and transplantation. Annu Rev Immunol 19, 225-252.
44. Sharpe, A. H., and Freeman, G. J. (2002). The B7-CD28 superfamily. Nat Rev Immunol 2, 116-126.
45. Smith, G. R., and Sternberg, M. J. E. (2002). Prediction of protein-protein interactions by docking methods. Curr Opin Struc Biol 12, 28-35.
46. Sobolev, V., Sorokine, A., Prilusky, J., Abola, E. E., and Edelman, M. (1999). Automated analysis of interatomic contacts in proteins. Bioinformatics 15, 327-332.
47. Szklarczyk, D., Franceschini, A., Kuhn, M., Simonovic, M., Roth, A., Minguez, P., Doerks, T., Stark, M., Muller, J., Bork, P., et al. (2011). The STRING database in 2011: functional interaction networks of proteins, globally integrated and scored. Nucleic Acids Res 39, D561-D568.
48. Tuncbag, N., Gursoy, A., Nussinov, R., and Keskin, 0. (2011). Predicting protein protein interactions on a proteome scale by matching evolutionary and structural similarities at interfaces using PRISM. Nat Protoc 6, 1341-1354.
49. Wai Wong, C., Dye, D. E., and Coombe, D. R. (2012). The role of immunoglobulin superfamily cell adhesion molecules in cancer metastasis. International journal of cell biology 2012, 340296.
50. Watanabe, T., Suda, T., Tsunoda, T., Uchida, N., Ura, K., Kato, T., Hasegawa, S., Satoh,
51. S., Ohgi, S., Tahara, H., et al. (2005). Identification of immunoglobulin superfamily 11 (IGSF11) as a novel target for cancer immunotherapy of gastrointestinal and hepatocellular carcinomas. Cancer Sci 96, 498-506.
52. Weber, J. (2007). Review: anti-CTLA-4 antibody ipilimumab: case studies of clinical response and immune-related adverse events. The oncologist 12, 864-872.
53. White, J. M., and Littman, D. R. (1989). Viral Receptors of the Immunoglobulin Superfamily. Cell 56, 725-728.
54. Xu, D., and Zhang, Y. (2009). Generating Triangulated Macromolecular Surfaces by Euclidean Distance Transform. Plos One 4.
55. Xue, F., Zhang, Y., Liu, F., Jing, J., and Ma, M. (2005). Expression of IgSF in salivary adenoid cystic carcinoma and its relationship with invasion and metastasis. Journal of oral pathology & medicine: official publication of the International Association of Oral Pathologists and the American Academy of Oral Pathology 34, 295-297.
56. Yan, Q. R., Malashkevich, V. N., Fedorov, A., Fedorov, E., Cao, E., Lary, J. W., Cole, J. L., Nathenson, S. G., and Almo, S. C. (2007). Structure of CD84 provides insight into SLAM family function. P Natl Acad Sci USA 104, 10583-10588.
57. Yap, E. H., Rosche, T., Almo, S., and Fiser, A. (2014). Functional Clustering of Immunoglobulin Superfamily Proteins with Protein-Protein Interaction Information Calibrated Hidden Markov Model Sequence Profiles. J Mol Biol 426, 945-961.
58. Yu, X., Harden, K., Gonzalez, L. C., Francesco, M., Chiang, E., Irving, B., Tom, I., Iveljia, S., Refino, C. J., Clark, H., et al. (2009). The surface protein TIGIT suppresses T cell activation by promoting the generation of mature immunoregulatory dendritic cells. Nat Immunol 10, 48-57.

What is claimed is:

1. A method for identifying a cognate ligand molecule for a known biological receptor comprised of amino acid residues, comprising:
   determining interaction energy map data for the known biological receptor, wherein the interaction energy data are determined for the known biological receptor with one or more predefined molecular entities;
   determining residue-specific pharmacophore data for the activity of the known biological receptor;
   generating ligand spatial interface structure data for the known biological receptor from combining the interaction energy map data and the pharmacophore data;
   and screening a candidate ligand molecule for binding to the generated receptor interface structure, and identifying the candidate ligand molecule as a cognate ligand molecule wherein the candidate ligand molecule binds to the generated receptor interface structure, or identifying the candidate ligand molecule as not being a cognate ligand molecule wherein the candidate ligand molecule does not bind to the generated receptor interface structure.

2. The method of claim 1, wherein the predefined molecular entity is a functional atom of a natural amino acid residue and is a carbon of a methyl group, nitrogen atom of lysine amino group or carboxyl oxygen atom of asparagine.

3. The method of claim 1, wherein the pharmacophore data for the activity of the known biological receptor is determined based on identifying, for amino acid residues of the known biological receptor, one or more of hydrogen bonding, an interactive side chain, a hydrophobic center, an aromatic center, and a charged region of the known biological receptor.

4. The method of claim 1, wherein the residue-specific pharmacophore data is determined by molecular dynamics sampling using single amino acid residue probes.

5. The method of claim 1, wherein the residue-specific pharmacophore data comprise one or more of hydrogen bonding, interactive side chain, hydrophobic and aromatic center data for the receptor.

6. The method of claim 1, wherein the residue-specific pharmacophore is built around the receptor interface based on optimal properties of functional atom types obtained from molecular dynamic sampling.

7. The method of claim 6, comprising using the properties of 26 functional atom types.

8. The method of claim 7, comprising using the properties of 26 functional atom types set forth in Table S1.

9. The method of claim 6, wherein optimal functional atom positions on the receptor interface are determined through sampling of single-residue ligand probes using molecular dynamics.

10. The method of claim 9, which comprises generating a 1 Å-mesh for each receptor interface.

11. The method of claim 10, wherein multiple molecular dynamic trajectories are launched at each mesh point for each single-residue probe type.

12. The method of claim 11, wherein functional atom positions are collected at 1-ps intervals from the trajectories and all functional atom positions that fall within 1A of any mesh point are assigned to that mesh point.

13. The method of claim 1, further comprising identifying candidate ligand molecules prior to screening them for binding, comprising extracting a template from the residue-specific pharmacophore and matching against a database of experimentally known or computationally modeled ligand structures so as to identify cognate receptor-ligand complexes, and subsequently using candidate ligand molecules corresponding to those identified complementary structures when screening for binding.

14. The method of claim 1, wherein the candidate ligand molecule is a 5-mer amino acid sequence.

15. The method of claim 1, wherein determining the residue-specific pharmacophore comprises selecting for residues where hydrogen bond donor-acceptor interactions exist and where hydrophobic contacts exist.

16. The method of claim 1, further comprising correcting the generated ligand spatial interface structure data for receptor surface protrusions and indentations.

17. The method of claim 6, comprising using the properties of 23 functional atom types.

18. The method of claim 7, comprising using the properties of the functional atom types set forth in Table S1 except for O_G, N_G and CB_C.

19. A system for identifying a cognate ligand molecule for a known biological receptor comprised of amino acid residues, comprising:
   one or more data processing apparatus;
   a graphical user interface; and
   a non-transitory computer-readable medium coupled to the one or more data processing apparatus having instructions stored thereon which, when executed by the one or more data processing apparatus, cause the one or more data processing apparatus to perform a method comprising:
      determining interaction energy map data for the known biological receptor, wherein the interaction energy data are determined for the known biological receptor with one or more predefined molecular entities;
      transmitting the interaction energy map data to a viewer application to cause a corresponding interaction energy map to display in the graphical user interface;
      determining residue-specific pharmacophore data for the activity of the known biological receptor;
      generating ligand spatial interface structure data for the known biological receptor from combining the interaction energy map data and the pharmacophore data;
      transmitting the ligand spatial interface structure data to the viewer application to cause display in the graphical user interface of the ligand interface structure as a visual combination of the displayed residue-specific pharmacophore and the displayed interaction energy map; and
      screening a candidate ligand molecule for binding to the generated receptor interface structure, and identifying the candidate ligand molecule as a cognate ligand molecule wherein the candidate ligand molecule binds to the generated receptor interface structure, or identifying the candidate ligand molecule as not being a cognate ligand molecule wherein the candidate ligand molecule does not bind to the generated receptor interface structure.

20. A non-transitory computer readable medium comprising instructions stored thereon for performing the method of claim 1.

* * * * *